US006174857B1

(12) United States Patent
Bürk

(10) Patent No.: US 6,174,857 B1
(45) Date of Patent: *Jan. 16, 2001

(54) COMPOSITION AND METHOD FOR THE TREATMENT OF OSTEOPOROSIS IN MAMMALS

(75) Inventor: Robert Roland Bürk, Bottmingen (CH)

(73) Assignee: Novartis Corporation, New York, NY (US)

(*) Notice: Under 35 U.S.C. 154(b), the term of this patent shall be extended for 142 days.

This patent is subject to a terminal disclaimer.

(21) Appl. No.: 08/774,510

(22) Filed: Dec. 30, 1996

Related U.S. Application Data

(63) Continuation of application No. 08/396,884, filed on Mar. 1, 1995, now Pat. No. 5,646,116, which is a continuation of application No. 08/252,061, filed on Jun. 1, 1994, now abandoned, which is a continuation of application No. 07/990,821, filed on Dec. 14, 1992, now abandoned, which is a continuation of application No. 07/686,309, filed on Apr. 16, 1991, now abandoned, which is a continuation of application No. 07/460,416, filed on Jan. 3, 1990, now abandoned.

(51) Int. Cl.$^7$ .......................... A61K 38/23; A61K 38/30; A61K 31/662; A61K 31/566

(52) U.S. Cl. ........................... 514/12; 514/108; 514/808; 514/874; 530/307; 530/303; 930/120

(58) Field of Search .............................. 514/12, 808, 108, 514/874; 530/307, 303; 930/120

(56) References Cited

U.S. PATENT DOCUMENTS

| | | | |
|---|---|---|---|
| 4,774,091 | * 9/1988 | Yamasira et al. | 424/426 |
| 4,876,242 | * 10/1989 | Applebaum et al. | 514/3 |

FOREIGN PATENT DOCUMENTS

| | | |
|---|---|---|
| 0123228 | 10/1984 | (EP). |
| 0289314A2 | 11/1988 | (EP). |
| 0318184 | 5/1989 | (EP). |

OTHER PUBLICATIONS

Bowie J U; Reidhaar–Olson J F; Lim W A; Sauer R T. Deciphering the message in proteinsequences: tolerance to amino acid substitutions. Science, (Mar. 16, 1990) 247 (4948) 1306–10.*

Russell S M; Spencer E M. Local injections of human or rat growth hormone or of purified human somatomedin–C stimulate unilateral tibial epiphyseal growth in hypophysectomized rats. Endocrinology, (Jun. 1985) 116 (6) 2563–7.*

Frost H M. Treatment of osteoporoses by manipulation of coherent bone cell populations. Clinical Orthopaedics and Related Research, (Sep. 1979) (143) 227–44.*

Schoenle, Eugen; Zapf, Juergen; Humbel, Rene E.; Froesch, E. Rudolf. Insulin–like growth factor I stimulates growth in hypophysectomized rats. Nature (London) (1982), 296(5854), 252–3.*

Reginster J Y; Deroisy R; Denis D; Lecart M P; Sarlet N; Franchimont P. Is there any place for salmon calcitonin in prevention of postmenopausal bone loss?. Gynecological Endocrinology, (Sep. 1988) 2 (3) 195–204.*

Am. J. Physiol. 250:E367–E372 (1986).

Annals of Internal Medicine, "Radiologic Methods to Evaluate Bone Mineral Content," 100:908–911 (1984).

Annals of Internal Medicine 104:874–876 (1986).

Bennett et al., "Characterization of Insulin–Like Growth Factor I Receptors on Cultured Rat Bone Cells: . . . ," Endocrinology 115(4):1577–1583 (1984).

Biochem. and Biophys. Res. Comm. (2):398–404 (1987).

Biochem. and Biophys. Res Comm. (2):672–679 (1987).

Biochem and Biophys. Res. Comm. 165(2):766–771 (1989).

Chiron Corporation Annual Report (1987).

Ebling et al., "Short–Term Effects of Recombinant Human Insulin–Like Growth Factor–I in Bone Turnover in Normal Women," Journal of Bone and Mineral Research vol. 7, Suppl. 1, Aug. 1992, Abstract 184, p. 5138.

Endocrinology 116(6):2563–2567 (1985).

Endocrinology 123(1):373–381 (1988).

Genant et al., "Osteoporosis: Assesment by Quantitative Computerized Tomography" Orthopedic Clinics of North America vol. 16, No. 3, Jul. 1985, 557–568.

Goffredsen et al., "Total Body Bone Mineral in Vivo by Dual Photon Absorptiometry," Clinical Physiology 4:343–355 (1984).

Guler et al., Proc. Natl. Acad. Sci. 85:4889–4893 (1988).

Hock, Chem. Abst. 88:154, abst. No. 50024e. (1988).

Hologic QDR™—1000 Product Literature, Aug. 1987.

Humbel, "Insulin–Like Growth Factors I and II," Eur. J. Biochem. 190:445–462 (1990).

J. Biological Chem. 261(13):5693–5695 (1986).

J. Biological Chem. 263(13):6233 (1988).

Journal of Bone and Mineral Res. vol. 6, Suppl. 1, Abstr. 549, p. F–221 (1991).

J. Clin. Endocrinol. and Metab., pp. 701–704 (1984).

J. Clin. Endocrinol. and Metab. 65(4):697–702 (1987).

J. Clin. Invest 66:709–719 (1980).

Johansson et al., "Insulin–Like Growth Factor I Stimulates Bone Turnover in Osteoporosis," The Lancet 339:1619 (1992).

Merimee, "Insulin–Like Growth Factors in Pygmies," The New England Journal of Medicine 316(15):906–911 (1987).

Metabolism 26(10):1079–1087 (1977).

(List continued on next page.)

Primary Examiner—David Romeo
(74) Attorney, Agent, or Firm—Gregory D. Ferraro

(57) ABSTRACT

Pharmaceutical compositions and methods for the treatment of osteoporosis in mammals are disclosed. The compositions are suitable for parenteral administration and comprise Insulin-Like Growth Factor I (IGF-I) and a pharmaceutically acceptable carrier. The compositions for use in the methods may also include bone antiresorptive compounds.

15 Claims, 6 Drawing Sheets

OTHER PUBLICATIONS

Mueller et al., "Insulin–Like Growth Factor–I IncreasesTrabecular Bone Mass in the Ovariectomized Rat," *J. Bone Mineral Research* Aug. 1991, vol. 6, Suppl. 1, Abstract 549, p. F–221.
*Orthopedic Clinics of North America* 16(3:557–568 (1985).
*Pediatric Research* 20(9):825–827 (1986).
*Proc. Natl. Acad. Sci.* 82:4535–4538 (1985).
*Proc. Natl. Acad. Sci.* 83:4904–4907 (1986).
Raisz, *New England Journal of Medicine* 318:818–823 (1988).
Schmid et al., "Insulin–Like Growth Factors Stimulate Synthesis of Nucleic Acids and Glycogen in Cultured Calvaria Cells," *Calcif. Tissue. Int.* 35:578–585 (1983).

Schoenle et al., "Comparison of In Vivo Effects of Insulin–Like Growth Factors I and II and of Growth Hormone in Hypophysectimized Rats," *Acta Endocrinologica* 106:167–174 (1985).
Schwander et al., "Synthesis and Secretion of Insulin–Like Growth Factor . . . ," *Endocrinology* 113(1):297–305 (1983).
Simpson, "Growth Factors Which Affect Bone," *Physiol.* 235 TIBS Dec. 1984.
*Stedman's Medical Dictionary*, 24th ed., Williams and Wilkins, Baltimore, p. 1301 (1982).
Wahner, "Assessment of Metabolic Bone Disease," *Mayo. Clin. Proc.* 60:827–835 (1985).

* cited by examiner

COMPOSITION AND METHOD FOR THE TREATMENT OF OSTEOPOROSIS IN MAMMALS

This application is a continuation of U.S. patent application Ser. No. 08/396,884, U.S. Pat. No. 5,646,116 filed Mar. 1, 1995, which is a Continuation of Ser. No. 08/252,061 filed on Jun. 1, 1994, abandoned which is a Continuation of Ser. No. 07/990,821 filed on Dec. 14, 1992, abandoned which is a Continuation of Ser. No. 07/686,309 filed on Apr. 16, 1991, abandoned which is a Continuation of Ser. No. 07/460,416 filed on Jan. 3, 1990, abandoned.

FIELD OF THE INVENTION

The present invention concerns a method for the treatment of patients having osteoporosis in which such patients exhibit decreased bone mineral density and patients substantially at risk of developing such decreased bone mineral density through the administration of insulin-like growth factor I (IGF-I) and pharmaceutical compositions therefor.

BACKGROUND OF THE INVENTION

Osteoporosis encompasses a broad range of clinical syndromes having varying etiologies. In postmenopausal women, for example, two distinct types of osteoporosis have been identified. Type I osteoporosis occurs mainly in the early postmenopausal period from about age 50–65. It is characterized by excessive resorption, primarily in trabecular bone. Vertebral fractures are common and if given prior to significant bone loss, treatment which decreases or prevents bone resorption (such as estrogen or calcitonin) is considered effective therapy.

Type II osteoporosis (a.k.a. senile osteoporosis) occurs essentially in all aging women and, to a lesser extent, in men. It is characterized by proportionate loss of cortical and trabecular bone. Here decreased bone formation plays a major role, if not a more important role than increased bone resorption. Fractures of the hip are characteristic of this type.

Currently approved therapeutic agents for osteoporosis are antiresorptives. As such, they are not as effective in patients with established osteoporosis of either type (decreased bone density with fractures of the vertebrae and/or hip), or in patients with Type II osteoporosis. In addition, the most accepted preventive agent for osteoporosis currently in use is estrogen therapy, which is not really an acceptable therapeutic agent for women with a history of breast cancer or endometrial cancer or for men with osteoporosis.

Insulin-like Growth Factor I (IGF-I) is a 70 amino acid peptide belonging to a family of compounds under the class name somatomedins and retains structural and biological similarities to insulin. The somatomedins activity lie on a spectrum from hypoglycemic effects similar to insulin to growth promoting effects which are exemplified by growth hormone. IGF-I predominantly induces growth and cell proliferation. IGF-I has also been demonstrated to specifically bind to receptors on rat osteoblast-like bone cells (Bennett et al, Endocrin. 115 (4): 1577–1583, 1984). IGF-I is routinely fabricated in the liver and released for binding to carrier proteins in the plasma (Schwander et al, Endocrin. 113 (1):297–305, 1983), which bound form is inactive. In addition, there is a biofeedback regulating loop involving the somatomedins and growth hormone such that higher somatomedin concentrations inhibit growth hormone release which results in lesser production of endogenous IGF-I.

IGF-I infused into rats has been shown to result in markedly greater increases in body weight gain compared to controls, with increases in tibial epiphyseal width and thymidine incorporation into costal cartilage (Nature 107: 16–24, 1984) and directly stimulate osteoblasts to result in a greater number of functional osteoblasts. IGF-I is also mentioned as the vehicle through which growth horrnone's effects on bone is mediated in Simpson, Growth Factors Which Affect Bone, Physiol. 235, TIBS, 12/84.

Nevertheless, it is important to note that the foregoing pre-clinical studies were conducted with fetal or newborn rat cells. It is highly likely that such "young" cells are more responsive to IGF-I (as well as other influences) than older cells, especially those in the elderly with established osteoporosis or those with drug or environmentally induced defects leading to reduced bone density.

Surprisingly, IGF-I has now been found to be useful in the treatment of osteoporosis in mammals exhibiting decreased bone mineral density and those exposed to drugs or environmental conditions which tend to result in bone density reduction and potentially to an osteoporosis condition.

Accordingly, an object of the present invention is to provide a method of treatment of osteoporosis in mammals exhibiting decreased bone mineral density and preventing osteoporosis due to bone mineral density reduction in patients who are clinically prone to such bone mineral density reductions.

Another object of the invention is to provide pharmaceutical compositions useful in achieving the foregoing object.

SUMMARY OF THE INVENTION

The present invention is directed to a method for, and composition useful in, the treatment of osteoporosis in patients demonstrating bone mineral density reductions and preventing such osteoporosis in patients prone thereto by administering to a patient having such osteoporosis or prone thereto an effective amount of IGF-I.

DETAILED DESCRIPTION OF THE INVENTION

The present invention concerns osteoporosis treatment and prevention, which osteoporosis is associated with decreased bone mineral density in mammals generally, but is especially suited for the treatment and prevention of such osteoporosis in humans.

IGF-I is a naturally occurring protein and can be obtained from a number of sources. Preferably, IGF-I from the same species, (or its synthetic twin) as is being treated therewith is employed but IGF-I from one species may be used to treat another species if the immune response elicited is slight or nonexistent. In addition, fragments of IGF-I having IGF-I activity, particularly IGF-I antiosteoporosis activity, are also suitably employed and unless the context of the disclosure clearly indicates otherwise, IGF-I as used herein is intended to include such active fragments. Where weights of IGF-I are presented, that weight of IGF-I and an approximately equipotent amount of active fragments is intended unless the text explicitly states otherwise. Where no type of IGF-1 is indicated, reference is to human –IGF-1 (meaning the structure, not the species source), unless the reasonable reading of the text indicates otherwise.

IGF-I can be synthetically produced, chemically or by recombinant techniques, although recombinant preparation is preferred. One such recombinant technique is disclosed in EP 123,228, incorporated herein by reference.

An effective amount of IGF-I is an amount sufficient to slow, stop, or reverse the bone mineral density reduction rate in a patient exhibiting bone mineral density reduction. In the Normal healthy 20–25 year old population bone mineral density in the spine (using dual photon densitometry) typically is in the range of 0.85 to 1.9 g/cm, usually 0.9 to 1.85 and most often 1.0 to 1.8; and in the mid radius and distal radius it is typically 0.7–1.4, usually 0.75–1.3, and most often 0.8–1.2 g/cm². Exemplary non-limiting normal ranges are shown in the Figures along with osteoporosis distributions. Norms using other techniques will be apparent from the literature and general experience therewith as experience with such techniques grow. Of course, it is to be remembered that different sub-populations have different norms in bone mineral density. For example Caucasian women typically differ in this parameter from Caucasian men as well as from black women, oriental women and women of other racial types. It is also important to remember that the current invention is directed to treating those with bone mineral density which is (a) totally below either the normal bone mineral density range for the population generally or for the patient sub-population or (b) below 1.0 g/cm³ or (c) below the fracture threshold (approximately 2 standard deviations below the mean bone mass for the population at age 35). The fracture threshold for the spine for example is defined as the bone mineral value below which 90% of all patients with one or more compression fractures of the spine are found (See Mayo Clin. Proc., Dec. 1985, Vol 60, p. 829–830). In addition, anyone who demonstrated a statistically significant reduction in bone density over a previous measurement, regardless of where that patient is in the typical ranges above, is a patient to whom the present invention treatment is directed. Statistical significance in this context will vary with the technique employed to measure bone mineral density, as well as with the sensitivity of the instruments used. However, with instrumentation and techniques generally available in 1988, a 1 or 2% change in bone mineral density from the earliest measurement to the most recent is not considered statistically significant. Still as techniques and equipment improve, persons of ordinary skill in the field of bone density measurement will revise downward the maximum percent change which is not considered statistically significant.

Current bone mineral density measurement techniques include dual energy radiography, quantitative computerized tomography, single photon densitometry, and dual photon densitometry. These techniques will be well known to those of ordinary skill in the art; however, descriptions thereof can be found in: *Mayo Clin. Proc., Dec.* 1985, Vol. 60, p. 827–835; *Orthopedic Clinics of North America,* Vol. 16, No. 3, July 1985, p. 557–568; *Hologic QDR™-1,000 Product Literature; Annals of Internal Medicine,* 1984, 100: p. 908–911; and *Clinical Physiol* 4:343, 1984.

Notwithstanding, the lack of statistical significance in a particular result, any bone mineral density reduction should be followed for further reductions, which cumulatively may be significant.

Usually, an effective amount of IGF-I, when given parenterally (intravenously, subcutaneously, intramuscularly, etc.), is between 2½ μg/Kg/day up to about 180 μg/Kg/day, preferably about 5 μg/Kg/day up to about 150 μg/KG/day, more preferably 10 μKg/day up to about 120 μg/Kg/day, even more preferably 20 μg/Kg/day up to about 100 μg/Kg/day, still more preferably about 30 μg/Kg/day up to about 90 μg/Kg/day. When given continuously, such effective amount may be given in two or three doses spread over time such as by IV drip or subcutaneous injection(s) with the total daily dose being spread across the portion or the entire administration period. Typical continuous dosing is in the range of about 2½ μg/Kg/hour up to about 50 μg/Kg/ hour, preferably about 5 μg/Kg/hour up to about 25 μg/Kg/hour, although wider ranges of "continuous" administration amounts will be apparent to those of ordinary skill. When given by subcutaneous injection, it is most preferably administered from 3 times/wk up to 3 times a day, preferably twice a week up to once or twice daily.

The specific dosage for a particular patient, of course, has to be adjusted to the degree of response, the route of administration, the individual weight and general condition of the patient to be treated, and is finally dependent upon the judgement of the treating physician.

In general the pharmaceutical preparations for use in the present invention comprise an effective amount of IGF-I or an active fragment thereof together with a pharmaceutically and parenterally acceptable carrier or adjuvant Compositions having an approximately 6 day supply typically contain from 0.1 mg to 15 mg, preferably 1 mg to 13 mg, more preferably about 3 mg to about 10 mg, most preferably 5 mg–10 mg of IGF-I. The liquid carriers are typically sterile water, approximate physiologic saline, 0.1 M acetic acid, 5% aqueous dextrose, etc.; preferably sterile water, physiologic saline, or 5% aqueous dextrose.

The carriers and adjuvants may be solid or liquid and may be organic or inorganic. The active compound and the compositions of the invention are preferably used in the form of preparations or infusions for parenteral (subcutaneous, intramuscular, or intravenous) administration. Such solutions are preferably isotonic aqueous solutions or suspensions which can be prepared before use, for example reconstituted from a lyophilised preparation. The pharmaceutical preparations may be sterilized and/or contain adjuvants, for example preservatives, stabilizers, wetting agents, emulsifiers, solubilizers, tonicity regulating salts, and/or buffers. Other adjuvants will of course be apparent to the ordinarily skilled formulation chemist.

The present pharmaceutical preparations, which, if desired, may contain further pharmacologically active or otherwise pharmaceutically valuable substances, especially bone antiresorptives such as estrogen, calcitonin, and bis-phosphonates particularly 3-aminopropyl-1-hydroxy-1,1-bisphosphonate are prepared from their constituent parts by techniques known in the art, for example lyophilization, dissolution, reconstitution, and suspension techniques, among others known to those of ordinary skill. They typically contain from about 0.1% to about 100% of active ingredient, especially in the case of solutions—about 1% to about 20% active ingredient and especially in the case of a lyophilizate—up to 100% of active ingredient.

DESCRIPTION OF THE DRAWINGS

FIGS. 1 and 2 are taken from the Mayo Clin. Proc., Vol. 60, Dec. 1985 reference mentioned herein and are themselves based on data from Riggs B L, Wahner H W, Dunn W L, Mazess R B, Offord K P, Melton L J III: Differential changes in bone mineral density of the appendicular and axial skeleton with aging: relationship to spinal osteoporosis. J. Clin. Invest. 67:328–335, 1981.

FIGS. 3–6 are taken from Orthopedic Clinics of North America, Vol. 16. No. 3, July 1985 reference mentioned herein.

Figure 1:
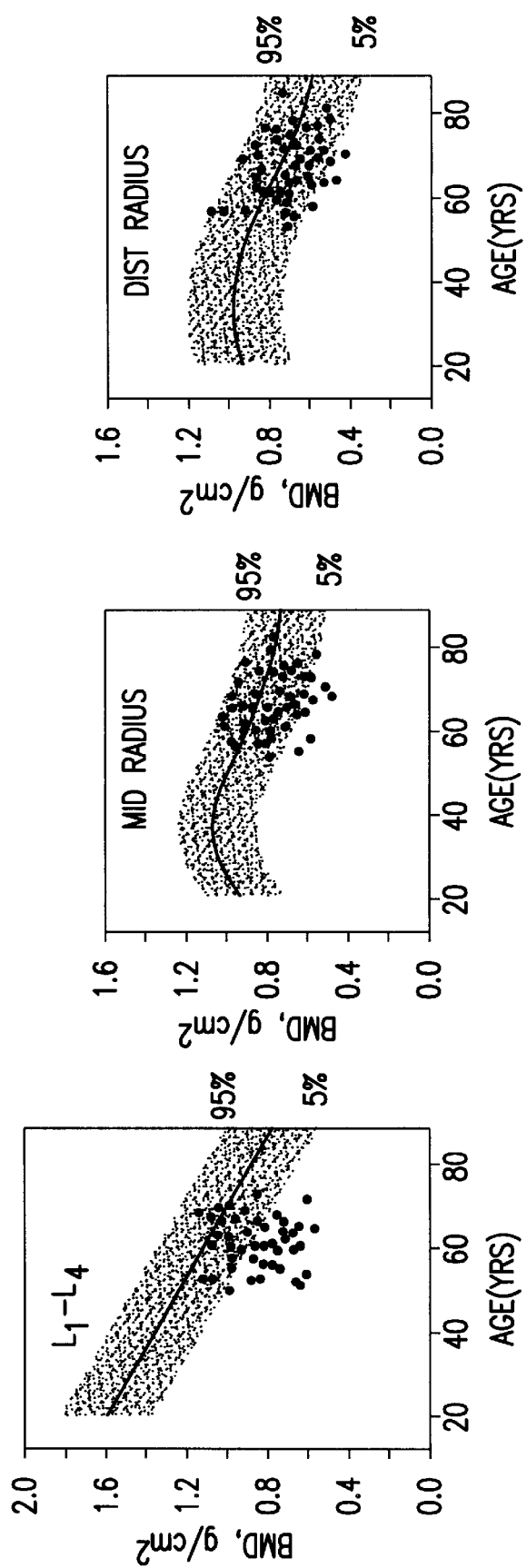
FIG. 1. Bone mineral density (BMD) in spine (L1-4; measured with use of dual-photon absorptiometry), midradius, and distal radius (measured with use of single-photon absorptiometry) in 76 women with osteoporosis in comparison with age- and sex-adjusted normal range (105) women). Shaded area represents 5th and 95th percentile range of normals. Patients with osteoporosis are indicated by dots. Note incomplete separation of the two populations. Spinal measurements result in the best distinction of patients with osteoporosis from normal subjects because this disease primarily affects trabecular bone of the spine.
Figure 2:
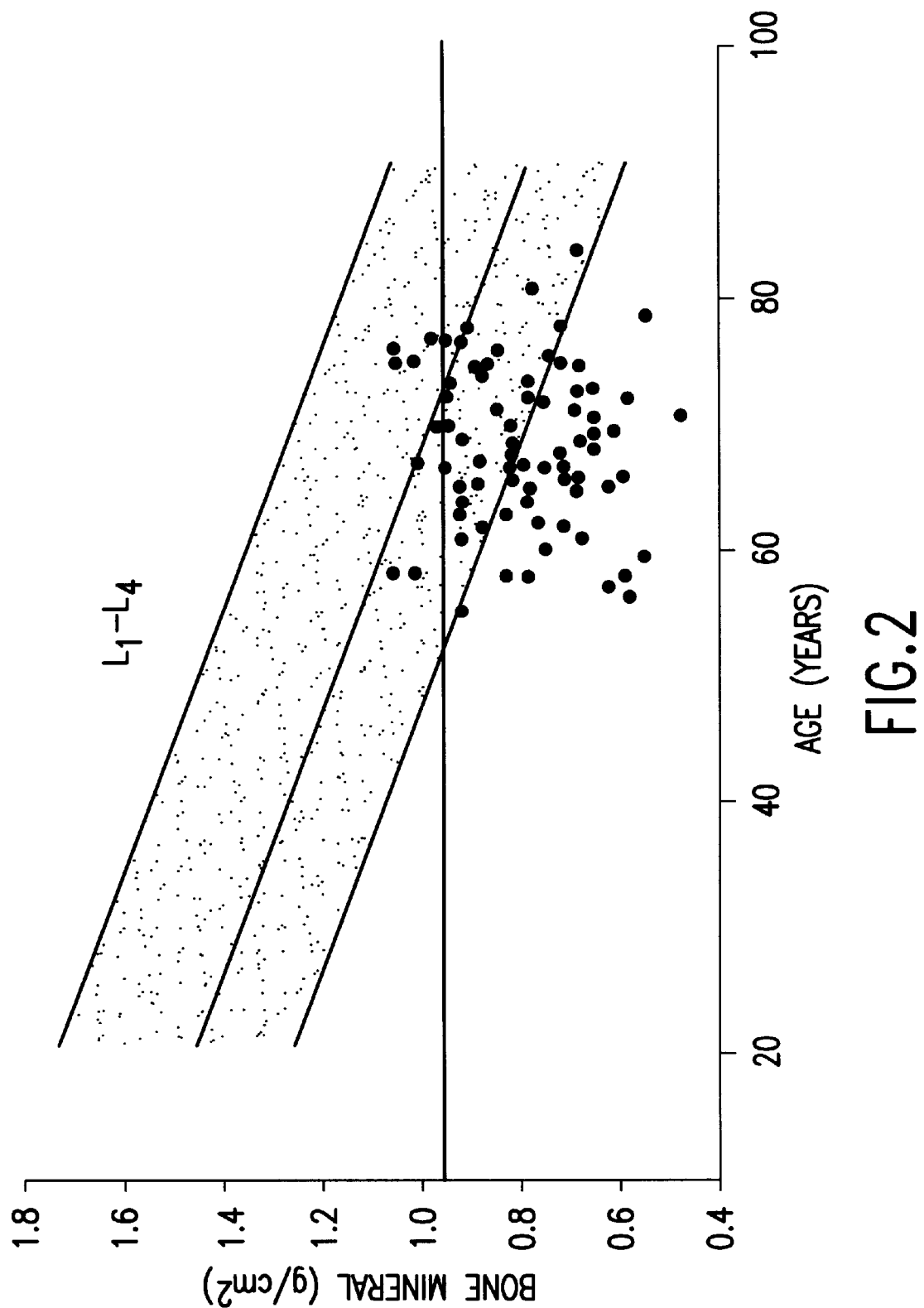
FIG. 2. Fracture threshold for spinal bone mineral (horizontal line) superimposed on normal range (shaded area) and values for 76 patients with osteoporosis (dots), as depicted in FIG. 1. With progressing age, values cf increasing numbers of normal subjects are below the fracture threshold. Fracture threshold is approximately two standard deviations below mean bone mass at age 35 years.
Figure 3A:
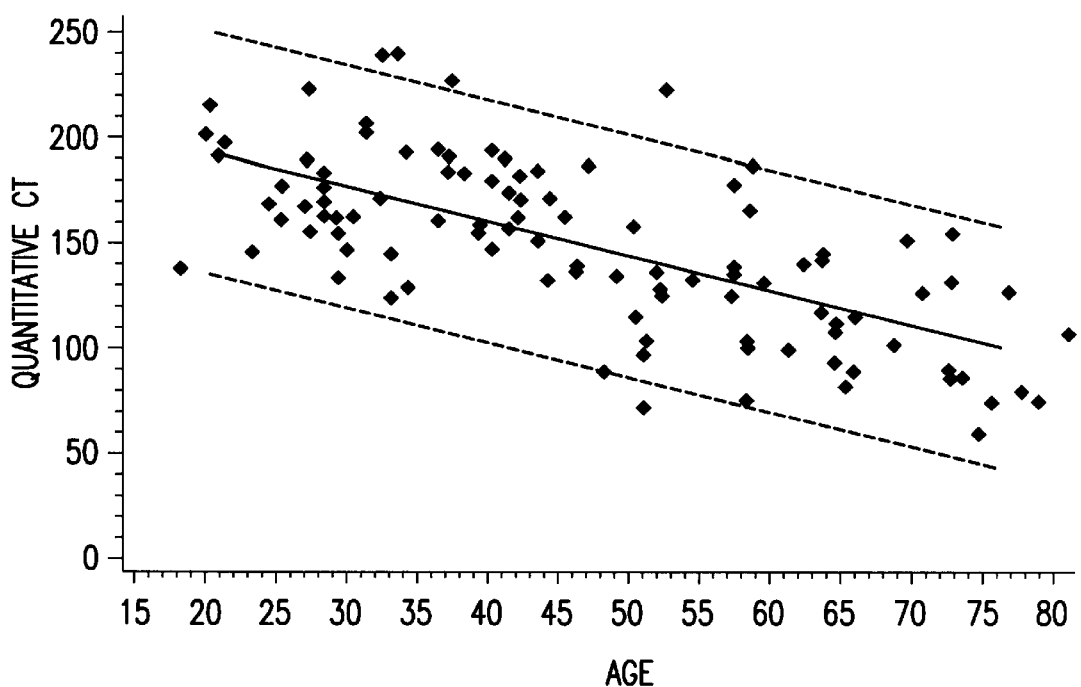
FIG. 3. A. Normal male values for vertebral cancellous mineral content by QCT. using a cubic regression with 95 percent confidence intervals. The cubic regression gives only a slightly better fit to the data for men than does a linear regression (p.<0.15). B. Normal female values for vertebral cancellous mineral content by QCT, using a cubic regression with 95 per cent confidence intervals (p.<0.05). An accelerated loss is observed after menopause.
Figure 3B:
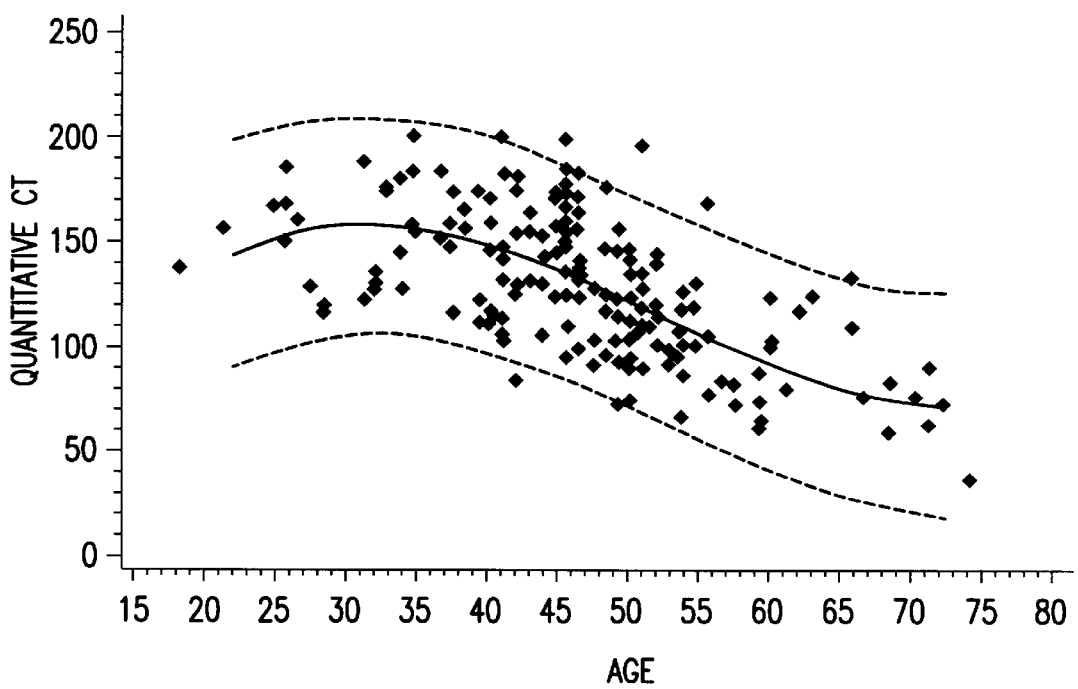
Figure 4A:
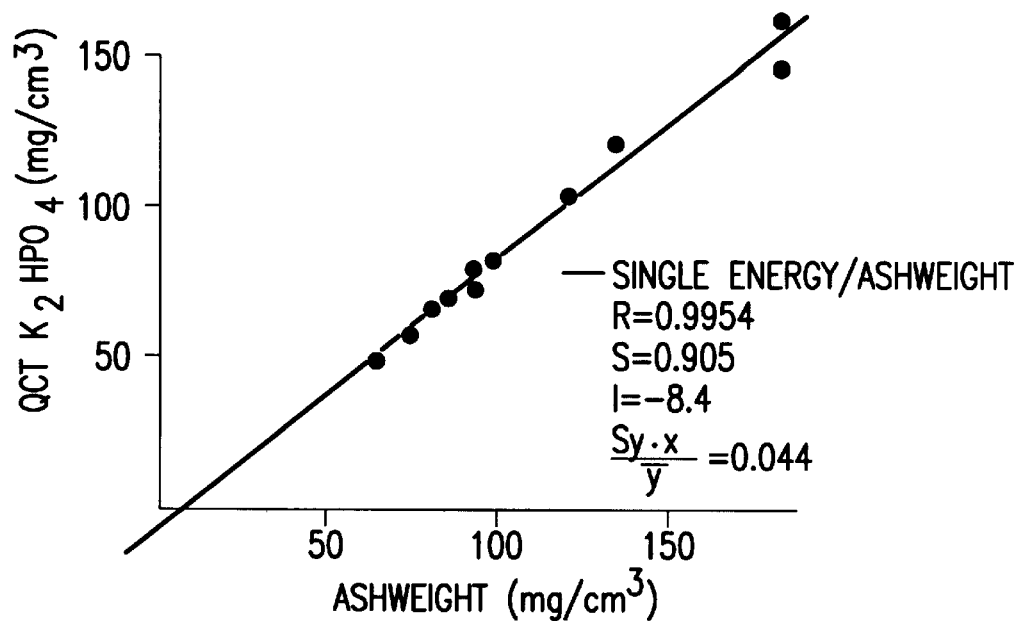
FIG. 4. A and B. The accuracy of single-energy QCT is shown for vertebral specimens (preserved in sodium azide) from 11 patients (10 men and 1 woman), ages 40 to 90 years.
Figure 4B:
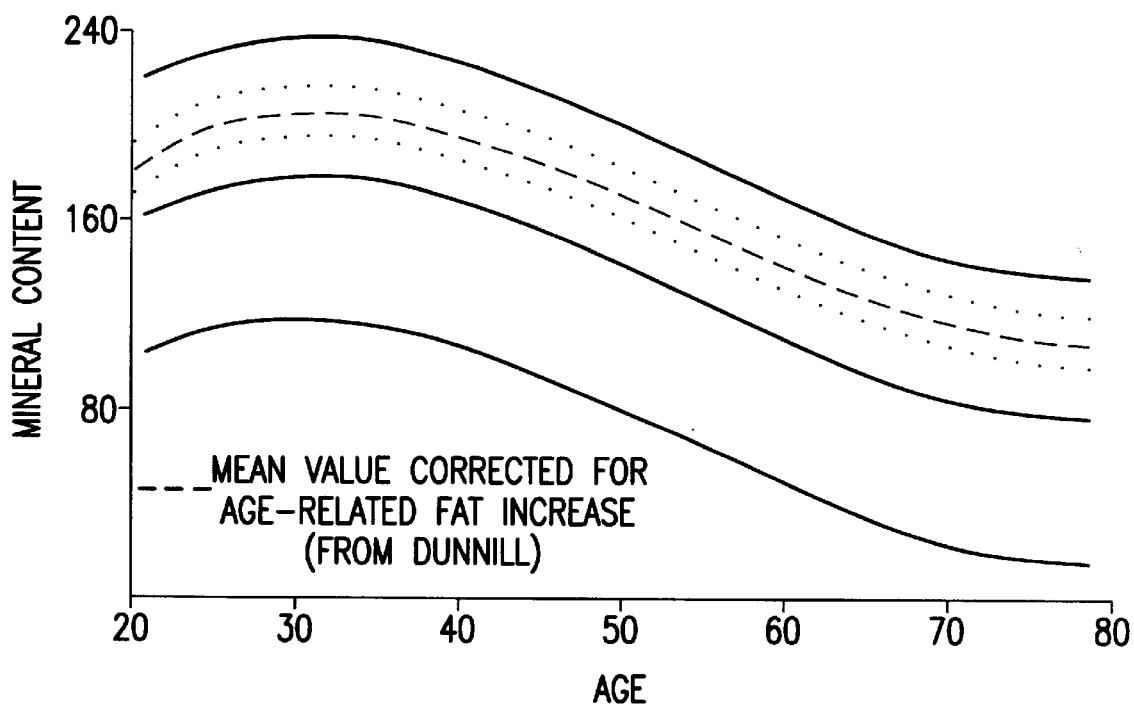
Figure 5:
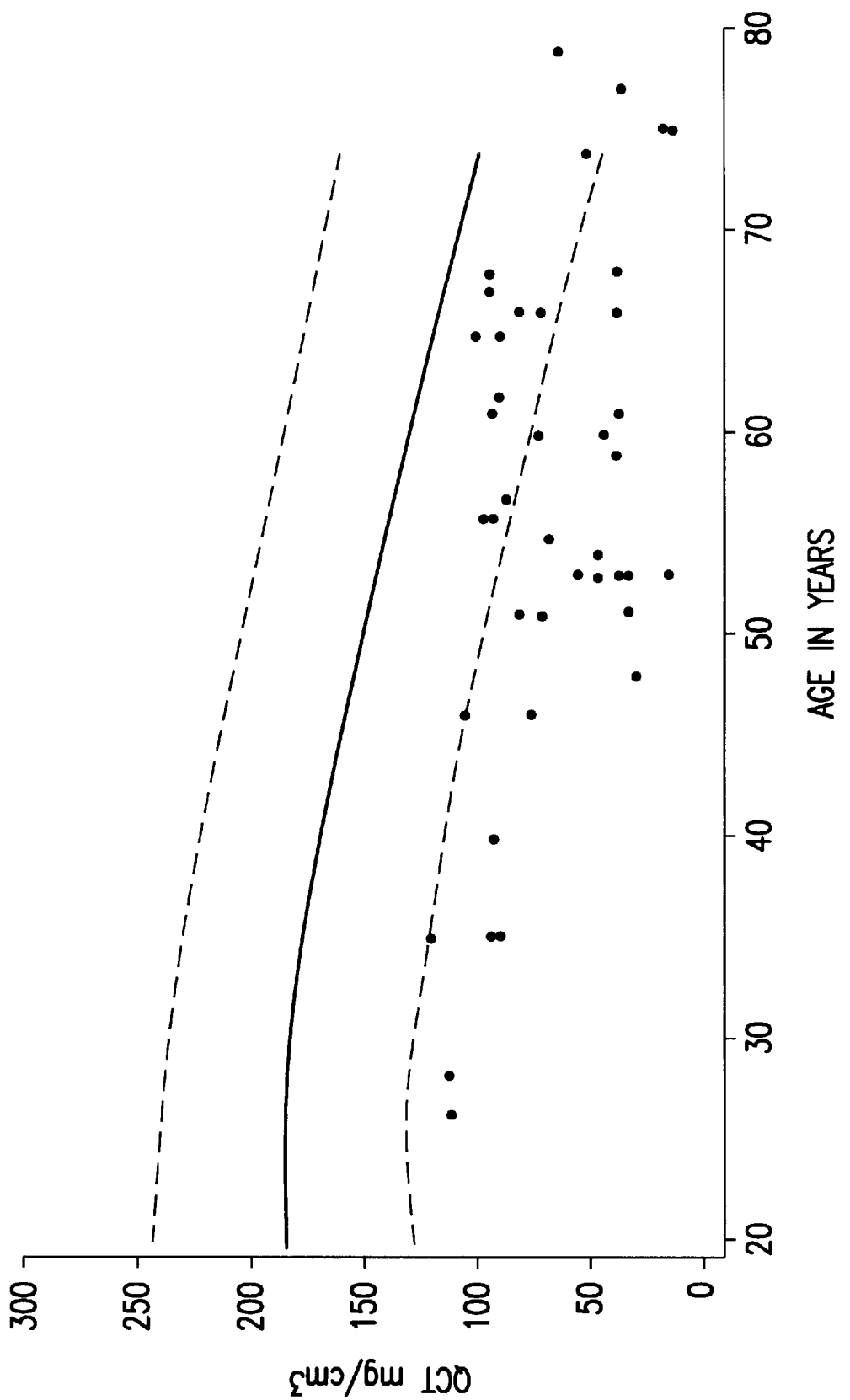
FIG. 5. Values for men with idiopathic osteoporosis and spinal fractures are plotted (black dots) against the normal male curve (cubic regression with 95 per cent confidence intervals). A fracture threshold at approximately 110 mg/cm$^3$ is observed.
Figure 6:
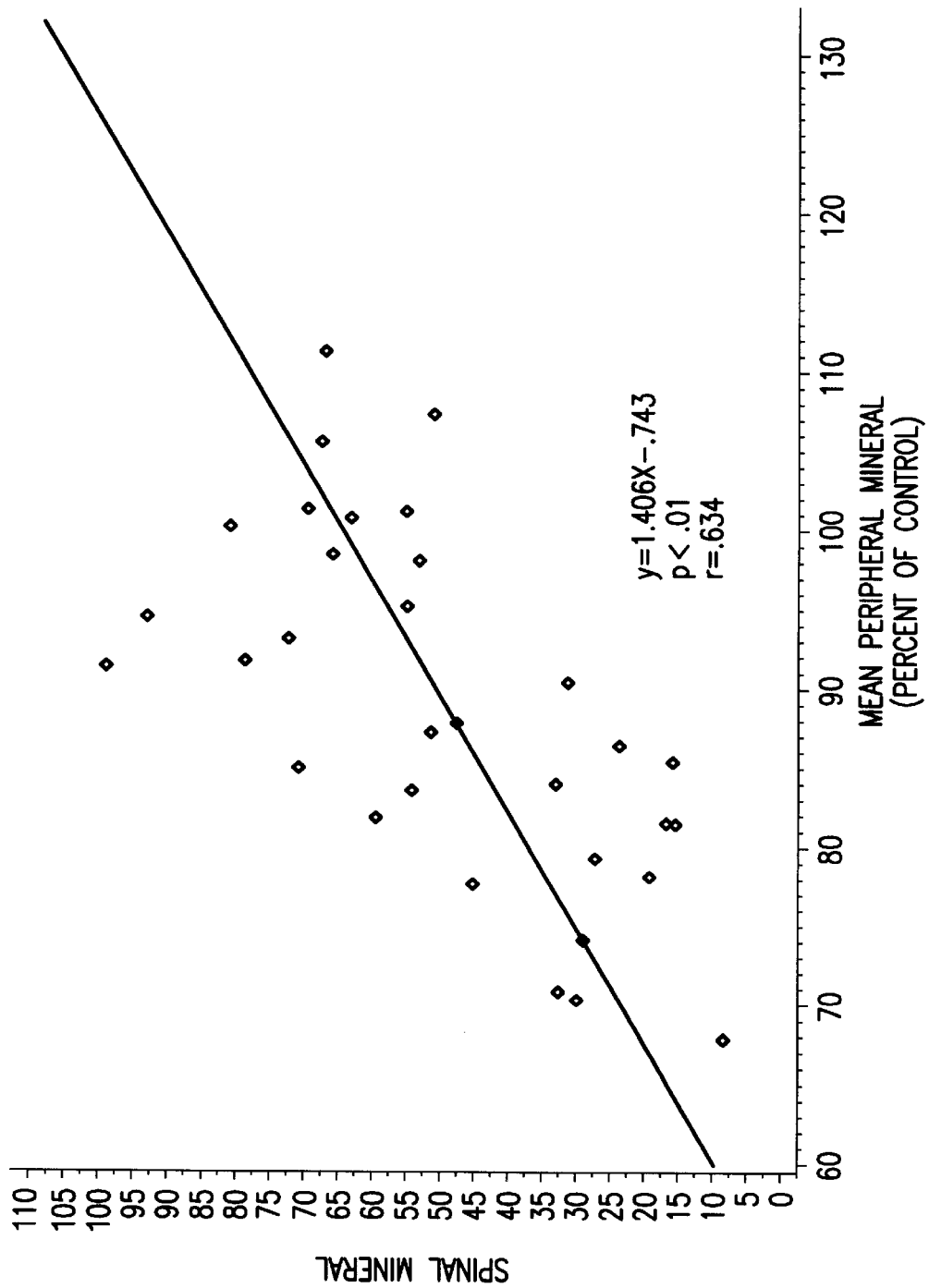
FIG. 6. Idiopathic osteoporotic male values showing larger decrement from normal for vertebral mineral QCT than for mean peripheral cortical mineral by radiogrammetry and photon absorptiometry.

Having fully described the instant invention, the following non-limiting Examples are presented to more clearly set forth the invention without limiting it.

EXAMPLES 1–3

Dry ampules of IGF-I:

Sterile, filtered 1% (w/v) aqueous solution of IGF-I is added, in the amount indicated to the respective dry amules the solution is then lyophilized to result in the dry ampules to be reconstituted shortly before use with the indicated amount of sterile water, physiologic saline, 0.1 M acetic acid, or 5% aqueous dextrose. Each vial is sufficient for a 6 day course of treatment for the intended patient.

|  | Ex 1 | Ex 2 | Ex 3 |
| --- | --- | --- | --- |
| ampule size | 5 ml | 8 ml | 50 ml |
| IGF-I fill volume | 1 ml | 5 ml | 30 ml |
| Reconstitution Volume | 1 ml | 5 ml | 30 ml |

What is claimed is:

1. A pharmaceutical composition suitable for parenteral administration for the treatment or prevention of osteoporosis in a mammal comprising:
   (a) Insulin-Like Growth Factor I (IGF-1) or an active fragment thereof, in an amount sufficient to prevent, slow, stop, or reverse the bone mineral density reduction rate in a mammal exhibiting bone mineral density reduction;
   (b) a bone antiresorptive effective amount of a bone antiresorptive compound; and
   (c) a pharmaceutically acceptable carrier.

2. The composition of claim 1 wherein said composition comprises IGF-1.

3. The composition of claim 2, wherein said mammal is a human being.

4. The composition of claim 2 wherein said IGF-I is human IGF-I.

5. The composition of claim 2 wherein said IGF-I is of natural origin.

6. The composition of claim 2 wherein said IGF-I is of synthetic origin.

7. The composition of claim 1 wherein said IGF-I is manufactured via recombinant technology.

8. The composition of claim 2 wherein said bone antiresorptive active compound is selected from an estrogen, a calcitonin, and a hydroxy-alkyl bisphosphonate.

9. The composition of claim 8 wherein said estrogen is conjugated estrogens or estradiol, said calcitonin is a human calcitonin, and said hydroxy-alkyl-bisphosphonate is 3-amino-propyl-1-hydroxy-1,1-bisphosphonate or a pharmaceutically acceptable salt thereof.

10. A method for the treatment of osteoporosis in a mammal having reduced bone mineral density or prevention thereof in a mammal prone thereto comprising administering to said mammal a composition according to claim 2, in an amount sufficient to prevent, slow, stop, or reverse the bone mineral density reduction rate in said mammal.

11. A method for the treatment of osteoporosis in a mammal having reduced bone mineral density or prevention thereof in a mammal prone thereto comprising administering to said mammal a composition according to claim 1, in an amount sufficient to prevent, slow, stop, or reverse the bone mineral density reduction rate in said mammal.

12. A method for the treatment of osteoporosis in a mammal having reduced bone mineral density or prevention thereof in a mammal prone thereto comprising administering to said mammal in need thereof an amount of Insulin-Like Growth Factor I (IGF-1) or an IGF-I active fragment of IGF-I, sufficient to prevent, slow, stop, or reverse the bone mineral density reduction rate in said mammal, and administering to said mammal a bone anti-resorptive amount of a bone anti-resorptive compound.

13. The method of claim 12, comprising administering to said mammal in need thereof an amount of IGF-1 sufficient to prevent, slow, stop, or reverse the bone mineral density reduction rate in said mammal.

14. The method of claim 13 wherein said administration of said IGF-I is in conjunction with said bone anti-resorptive compound treatment.

15. The method of claim 13 wherein said administration of said IGF-I and said bone anti-resorptive treatment are by different routes of administration.

* * * * *